United States Patent [19]

Orr et al.

[11] Patent Number: 4,869,262

[45] Date of Patent: Sep. 26, 1989

[54] DEVICE FOR DISPLAYING BLOOD PRESSURE

[75] Inventors: Thomas Orr, Lee-on-the-Solent; Malcolm E. Carruthers, London, both of England

[73] Assignee: Pulse Time Products Limited, West Sussex, England

[21] Appl. No.: 194,176

[22] Filed: May 16, 1988

Related U.S. Application Data

[63] Continuation of Ser. No. 9,891, Feb. 2, 1987.

[51] Int. Cl.$^4$ .................................................. A61B 5/02
[52] U.S. Cl. .................................... 128/672; 128/687; 128/700
[58] Field of Search ......................... 128/672, 677–690, 128/696, 700, 708

[56] References Cited

U.S. PATENT DOCUMENTS

| | | | |
|---|---|---|---|
| Re. 27,042 | 1/1971 | Jorgensen et al. | 128/700 |
| 3,132,643 | 5/1964 | Baum et al. | |
| 3,939,824 | 2/1976 | Arneson et al. | 128/672 |
| 4,137,910 | 2/1979 | Murphy | 128/700 |
| 4,185,621 | 1/1980 | Morrow | |
| 4,216,779 | 8/1980 | Squires et al. | 128/708 X |
| 4,245,648 | 1/1981 | Trimmer et al. | |
| 4,425,921 | 9/1981 | Fujisaki et al. | 128/690 |
| 4,446,872 | 5/1984 | Marsoner et al. | 129/700 |
| 4,478,224 | 10/1984 | Bailey | 128/708 X |
| 4,489,731 | 12/1984 | Baumberg | 128/690 |

FOREIGN PATENT DOCUMENTS

| | | |
|---|---|---|
| 0021800 | 1/1981 | European Pat. Off. |
| 2537485 | 4/1976 | Fed. Rep. of Germany |
| 2058355 | 4/1981 | United Kingdom |

OTHER PUBLICATIONS

Carruthers et al., "Validation of a New, Inexpensive, Non-Invasive Miniaturized Blood-Pressure Monitor", J. of Ambulatory Monitoring, 1988, vol. 1, No. 2.

Primary Examiner—Kyle L. Howell
Assistant Examiner—Angela D. Sykes
Attorney, Agent, or Firm—Watson, Cole, Grindle & Watson

[57] ABSTRACT

A measure of diastolic blood pressure is provided by the product of HR and TT wherein HR is a measured heart beat rate and TT is an elapsed time between emission of an electrocardiographic R wave and arrival of the consequent blood pressure pulse at a chosen blood vessel.

Apparatus is disclosed for sensing HR and TT and displaying a value or index of diastolic blood pressure, which is intended to be worn on the wrist and may serve also as a timepiece.

5 Claims, 4 Drawing Sheets

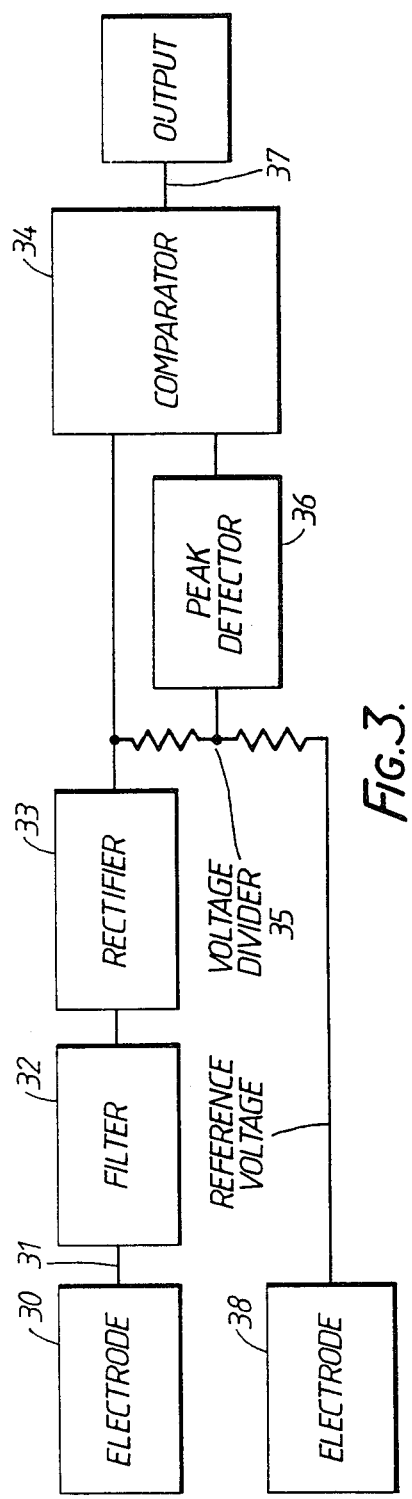
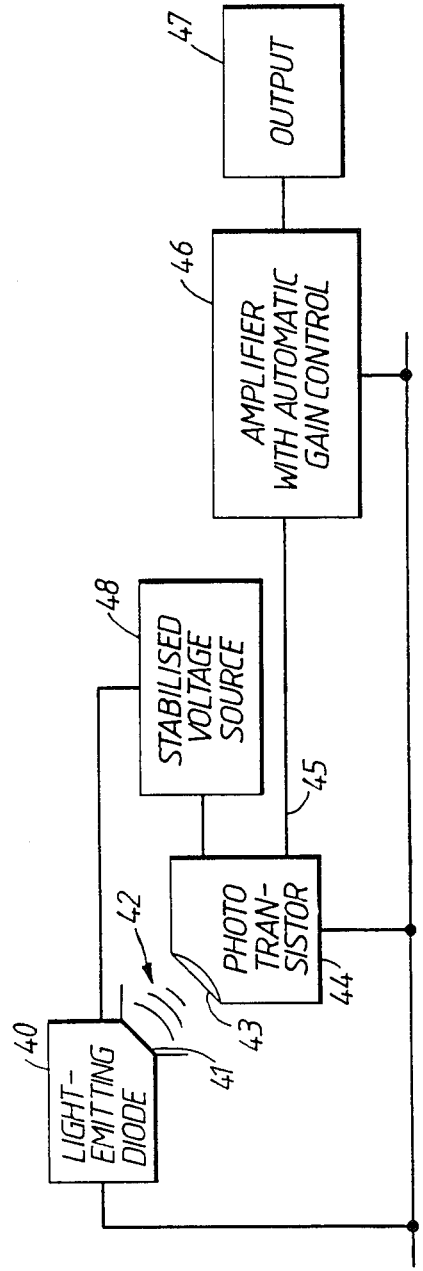

DEVICE FOR DISPLAYING BLOOD PRESSURE

This application is a continuation application of application Ser. No. 009,891, filed Feb. 2, 1987, now abandoned.

BACKGROUND OF THE INVENTION

1. Field of the Invention

The present invention relates to a method of, and device for, displaying a value or index of blood pressure within a living human or animal body which method includes the steps of sensing the emission of electrocardiographic R-waves, sensing the arrival of consequent pulses of blood at a chosen blood vessel and computing (i) an elapsed time TT between the sensed instant of emission of each R-wave and the sensed instant of arrival of the consequent pulse, and (ii) a heart beat rate HR, being a sensed number of R-waves occurring in a given unit of time.

2. Description of Related Art

Such a method is described in European patent application No. EP-A-0021800, which also discloses apparatus for carrying out such a method, but the disclosure concerns only the monitoring and display of a generalised blood pressure, not indicative of an underlying diastolic blood pressure. Strenuous exercise has a general effect of raising systolic blood pressure and heart rate, but has less effect on diastolic blood pressure.

In the field of preventative medical treatment of heart disease, there has long been a necessity for routine long term monitoring of diastolic blood pressure without significant disturbance of the ordinary life of the subject.

SUMMARY OF THE INVENTION

It is one object of the present invention to provide a method of indicating in real time at least one of (i) changes in, and (ii) absolute values of, diastolic blood pressure, using data obtained from personal portable sensing apparatus.

According to a first aspect of the present invention there is provided a blood pressure display method as hereinbefore defined, and characterised by the steps of: (a) finding the product of HR and TT; (b) computing a value or index of diastolic blood pressure as a function of the said product (HR.TT); and (c) displaying the said value or index.

According to a second aspect of the invention, there is provided a device for displaying a blood pressure value or index for a living human or animal body comprising means for detecting electrocardiographic R-waves, means for sensing the arrival at a chosen blood vessel of the consequent pulse of blood, means for computing an elapsed time TT between the sensed instant of emission of each R-wave and the sensed instant of arrival of the consequent pulse, and a heart beat rate HR being a sensed number of R-waves occurring in a given unit of time, and characterised by computing means programmed to generate as output the value of a stored function of the product HR.TT, and means to display a value or index of diastolic blood pressure based on said output value.

Underlying the present invention is an appreciation by the applicants, deriving from their own experiments and observations, that the diastolic blood pressure of any particular individual remains substantially unchanged irrespective of the degree of exercise or stress to which the body is subject, unlike the systolic pressure which tends to increase in proportion to the degree of exercise. It will be appreciated that, under stress, HR increases but TT falls. Thus, the product HR.TT changes less than either TT or HR.

Preferably the function on which the computing step is performed is F1 below:

$$DBP = m \cdot TT \cdot \frac{HR}{HR_c} + I \ldots F1$$

wherein m, $HR_c$ and I are all numerical constants and, more particularly:

m is the gradient of best fit of a straight line plot of the variation of absolute diastolic blood pressure (ordinate) against (TT.HR/HRc) (abscissa), m usually having a value of around −0.06 mmHg/ms and TT being usually in a range of from 100 to 300 ms;

I is the notional intercept of the straight line of gradient m with the said ordinate, the intercept usually having a value of some tens of millimeters of mercury.

$HR_c$ is a constant which represents an at rest heart beat rate; and

DBP is a displayed value of diastolic blood pressure, conveniently expressed in units of mm.Hg, normally of a value a little below 100.

The value of DBP changes relatively little with stress or exercise. The experiments which the applicants have conducted have provided empirical evidence of the truth of the formula F1.

The calibration constants m and I can be determined, for any particular subject, by measurements on that subject using an absolute diastolic blood pressure meter i.e. a sphygmomanometer. The calibration constant $HR_c$ can be determined using any convenient method of establishing an at-rest heart beat rate.

Real time measurements of current heart beat rate HR can be determined in the way described in the European patent application mentioned above, or in any other convenient manner.

Elapsed time TT again can be measured as described in the European patent application. It is, however, not entirely straightforward to obtain an accurate measurement of TT, because of the relatively slow rate of rise of blood pressure in the blood vessel upon arrival of the blood pressure pulse. One convenient way of determining the moment of arrival of the pulse is to establish the pressure of the peak of the pulse, the minimum pressure in the trough immediately preceding the pulse, and then to establish what is the time of arrival in the blood vessel of a blood pressure which is mid-way between the measured peak pressure and the trough pressure. Because the rate of change of pressure in the pulse at this point in the pressure curve is relatively fast, any given inaccuracy in measurement of the peak and trough pressures will give rise to only a very small inaccuracy in the calculated time of arrival of the median pressure.

Apparatus in accordance with the invention, which is preferably personal and portable has means to sense cardiographic R-waves and pulses of blood, and means to compute the quantities TT and HR as defined above, and preferred embodiments are characterised by means to compute DBP as defined above, from TT and HR, in accordance with formula F1. Changes of diastolic blood pressure from an "at rest" origin can be displayed graphically on the basis of measured values of TT, HR and $HR_c$ by using an assumed value of m. Absolute values can be displayed if the device is calibrated at two points on the straight line plot of F1, thereby to fix m and I for the specific subject under test.

In one embodiment, the apparatus might be in the form of a device worn on the wrist, and in another it is a small hand-held device. It is convenient for the step of sensing the arrival of the blood pressure pulse to be conducted in relation to a blood vessel in a thumb or fingertip of the subject.

It is convenient to provide the apparatus with means to display not only one or both of an indication of changes in diastolic blood pressure and an absolute diastolic blood pressure, but also a numerical indication of systolic blood pressure and/or heart beat rate. Preferably, the device provides a display of time or of further functions, such as those now provided as a matter of routine in microprocessor-based timepiece devices, so that it can display heart performance recovery data following, for example, as specified exercise programme.

BRIEF DESCRIPTION OF THE DRAWINGS

Reference will now be made, by way of example, to the accompanying drawings, in which:

FIG. 3 is a block diagram of the electrical pulse sensor of a preferred embodiment of the invention;

FIG. 4 is a block diagram of the pressure pulse sensor of the said embodiment;

DESCRIPTION OF A PREFERRED EMBODIMENT

Figure 1:
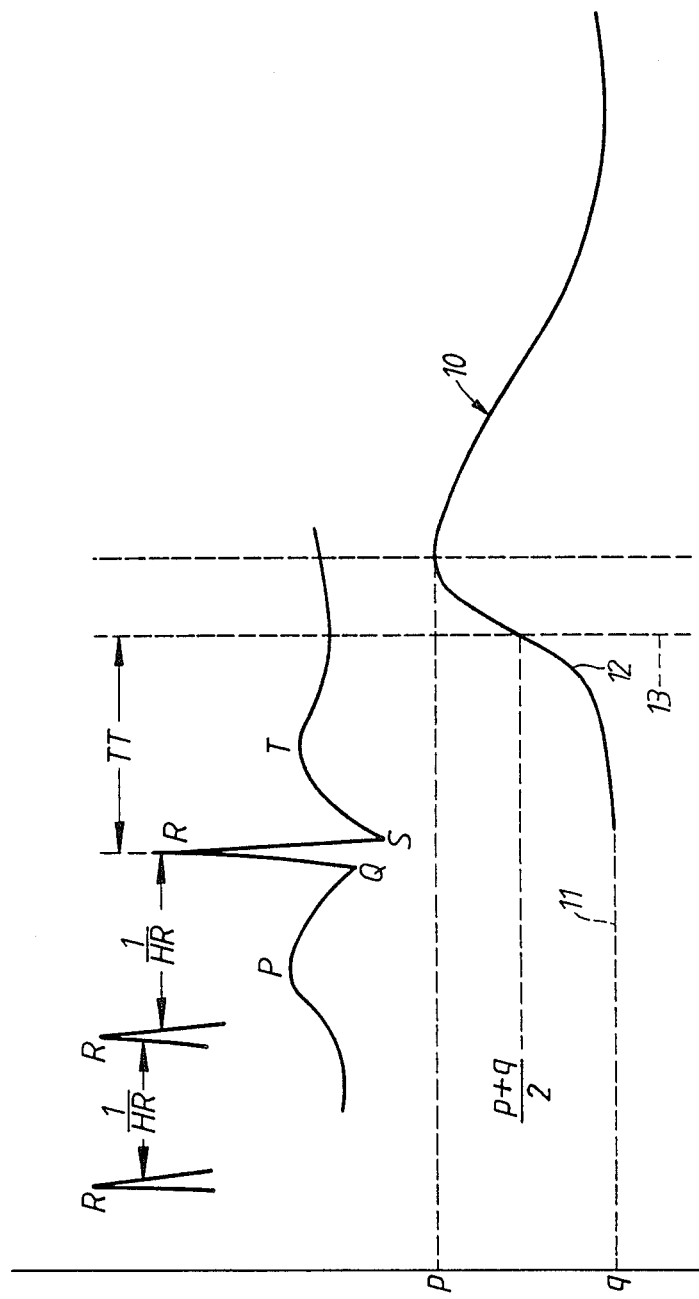
FIG. 1 shows schematically the form of electrical and blood pressure pulses characteristic of a beating heart.

Referring to FIG. 1, each electrical pulse (R-wave) is identified, as is conventional, with the letters PQRST wherein R identifies the sharp peak of the pulse. The frequency of such pulses is HR. The abscissa of the FIG. 1 graph represents time, so the horizontal distance between successive peaks R is 1/HR.

The blood pressure pulse 10 shows a period 11 of steady pressure q ahead of the pulse, a period 12 of rapidly rising pressure and a peak pressure p. One convenient way of determining the instant 13 of arrival of the pulse 10 is to define it as the instant when the pressure is $(p+q)/2$. As can be seen from FIG. 1, TT is the delay from the instant of the electrical peak R to the consequent instant 13 of arrival of the pressure pulse 10 at the blood vessel where the pressure is being sensed.

Figure 2:
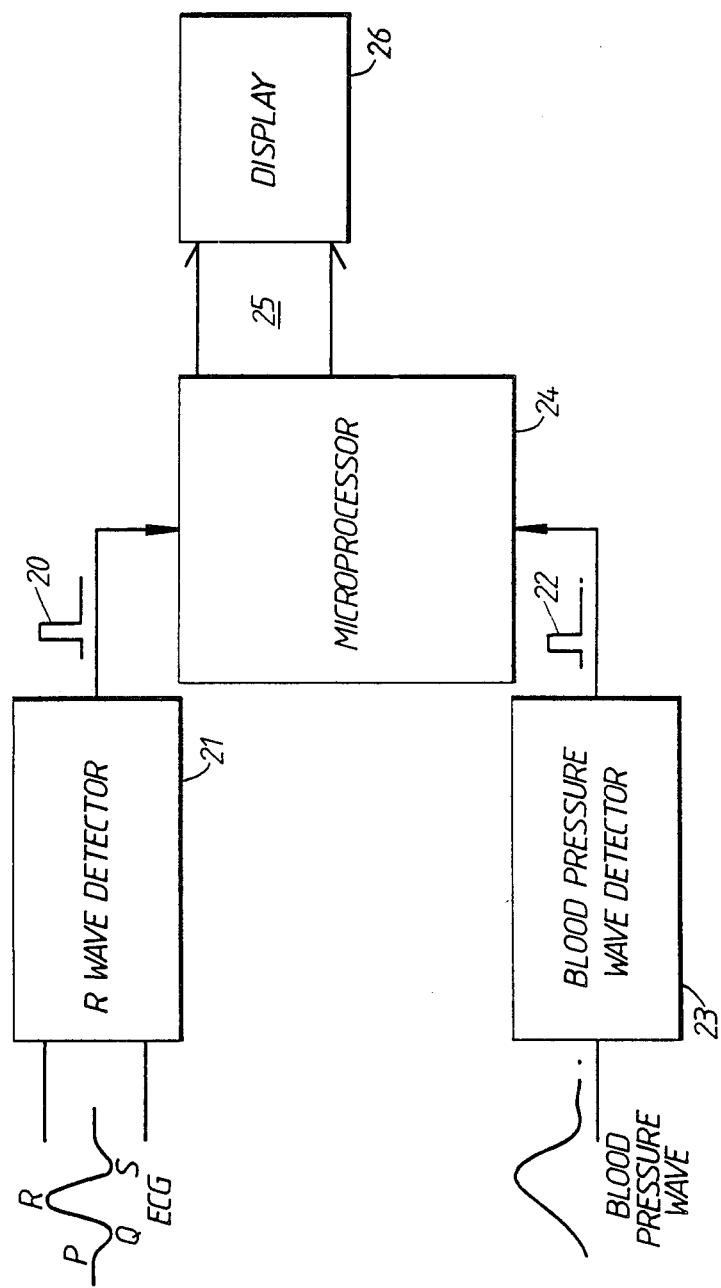
FIG. 2 is a block diagram of components of a device in accordance with the present invention.

FIG. 2 shows how a signal 20 from an R-wave sensor 21, and a signal 22 from a pressure sensor 23, are inputted to a microprocessor 24, the output 25 of which is delivered to a display means 26.

FIG. 3 shows the R-wave sensor 21 in greater detail. A first skin-contact electrode 30 outputs a signal 31 through a three stage band-pass filter 32 and a full-wave rectifier 33 to a comparator 34 and a voltage divider 35. The divider 35 inputs a peak detector 36 which provides a second input to the comparator 34, which generates an output signal 37 whenever the instantaneous signal from the electrode 30 exceeds 0.83 of the magnitude of the average signal from the electrode. A reference electrode 38 provides a reference voltage to the divider 35.

FIG. 4 shows how a light-emitting diode 40 provides illumination 41 to an area 42 of skin of the human body being monitored, the intensity of consequent illumination 43 of an adjacent phototransistor 44 varying with pressure of blood in vessels immediately below the area 42 of skin. The output 45 from the transistor is delivered to an amplifier 46 with automatic gain control, and its output 47 inputs the microprocessor 24. The diode 40, transistor 44 and amplifier 46 are all powered from a stabilised voltage source 48.

Figure 5:
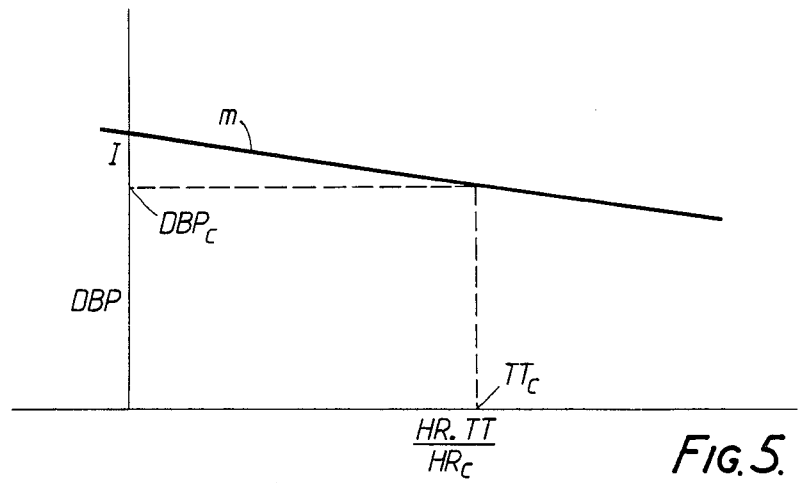
FIG. 5 is a graph of fuction F1.

FIG. 5 shows a graph showing the linear variation of DBP with the quantity $(HR.TT)/HR_c$. The gradient m is usually negative and of the order of $-0.06$. By measuring an "at rest" heart beat rate $HR_c$, and an elapsed time TTc at that instant, one can display an "index" of diastolic blood pressure with the origin DBPc of the index (conveniently displayed as the origin of a bar graph) at the moment of setting the "at rest" rate, and an assumed gradient m of, say, $-0.06$ mmHg/ms. Otherwise, one can calibrate the device, to find a real gradient m and intercept I, so allowing measured values of DBP to be displayed.

Figure 6:
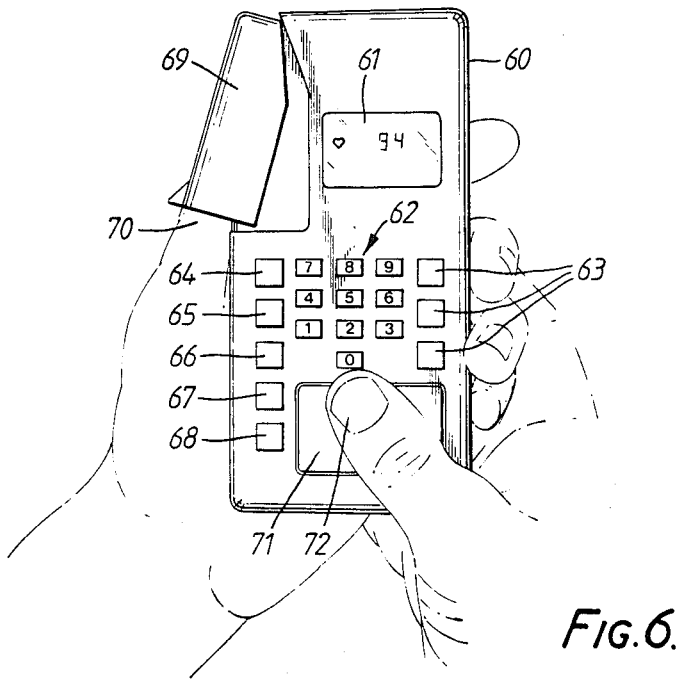
FIG. 6 is a perspective view of the said embodiment.

FIG. 6 shows the device in use. The circuits of FIGS. 2 to 4 are contained within a casing 60 in which is a display panel 61. A conventional numeric key pad 62 and chronometer keys 63 are provided. The functions of the five other keys, namely, ENTER 64, SET 65, AUDIO/SPLIT 66, MODE 67 and CAL 68 are briefly described below. Within a cuff 69 is a sensing element comprising an LED 40 and phototransistor 44 arrangement, as shown schematically in FIG. 4, for sensing the arrival of pulses of blood pressure in the tip of a digit 70 pressed against the sensing element within the cuff 69. A conductive area 71 on the front of the casing 60 is used to sense ECG R-waves in another digit 72 of the subject.

In use, the MODE key 67 is used to select one of the following modes: CHRONO, PRESSURE INDEX, PRESSURE VALUE. Use in the CHRONO mode is conventional and so will not be described.

In PRESSURE INDEX (PI) mode, pulse rate HR in beats/minute is displayed in the panel 61, as well as a bar graph showing the magnitude of both systolic and diastolic blood pressures relative to "at rest" values. To input the microprocessor with new "at rest" values, the CAL key 68 is depressed during monitoring. Relative values are computed and displayed on the basis of an assumed value of gradient m.

The device has an audio output (not shown) which can be actuated by depressing the AUDIO key 66 to signal each heart beat. Furthermore, the SET key 65 can be used to input numerical heart rate minimum and maximum values at which the audio output will sound an alarm. Using this facility an exercise programme can be pursued in which heart rate is maintained within a specified band of elevated heart rates. The function is continued so long as the conductive area 71 receives ECG signals. A digit 70 in the cuff 69 is not needed. By invoking the CHRONO mode a heart beat recovery time can be determined.

In PRESSURE VALUE (PV) mode, the device requires calibration. For this, the actual heart rate is noted and then, in PV mode, the CAL key 68 is depressed and at "at rest" numerical reference display value noted. Simultaneously, a sphygmomanometer is used to measure absolute values of diastolic and systolic blood pressure. The calibration procedure is repeated immediately following exercise, to obtain equivalent values at a higher heart rate.

Once these values are established they are inputted to the microprocessor by depressing the SET key 65 and depressing numeral keys as prompted by the display 61. As in the PI mode, specified limit values can be entered which, when reached, cause an audible warning to be emitted.

We claim:

1. A device for determining blood pressure for a living subject, comprising:
   a portable housing including a cuff member for receiving a digit of said subject for sensing the arrival of a pulse of blood and means for detecting electrocardiographic R-waves and including a conductive area adapted to receive another digit of said subject;
   means for displaying at least one of the pulse rate and the magnitude of systolic and diastolic blood pressure relative to at rest values;
   switching means for controlling the function of said device and including a respective switch for an enter, set, audio/split, mode and calibrate functions; and
   processing means for determining a value of diastolic blood pressure and including means for determining an elapsed time TT between the sensed instant of emission of each R-wave, the sensed instant of arrival of the consequent electrocardiographic R-wave and a heart beat rate HR, and means for computing the product of HR and TT and a constant having a value of blood pressure as a function of the product of HR and TT and determining said value of diastolic blood pressure.

2. A device according to claim 1, wherein said means for detecting electrocardiographic R-waves includes an electrode for contacting the skin of said digit and generating an electrical signal representative of the R-wave, means for band-pass filtering said electrical signal, means for rectifying the filtered electrical signal, means for determining the peak value of the rectified signal, and means for comparing said peak value with the instantaneous value of the rectified signal and producing an output when said instantaneous rectified signal is a predetermined percentage of said peak value.

3. A device according to claim 1, wherein said cuff member includes a light emitting diode and a phototransistor measuring the light varying with pressure of blood in said other digit to generate a signal representative of the blood pressure.

4. A device according to claim 1, wherein said computing means determines the end of the elapsed time TT as the instant when the increasing blood pressure marking the arrival of a pulse attains a value mid-way between the steady pressure preceding the pulse and the peak pressure attained during the pulse.

5. A device according to claim 1, wherein the computing means computes a value of systolic blood pressure based on the sensed value of TT.

* * * * *